United States Patent
McAuliffe et al.

(10) Patent No.: US 7,361,731 B2
(45) Date of Patent: Apr. 22, 2008

(54) PEPTIDE DERIVATIVES, AND THEIR USE FOR THE SYNTHESIS OF SILICON-BASED COMPOSITE MATERIALS

(75) Inventors: Joseph C. McAuliffe, Sunnyvale, CA (US); Risha Lindig Bond, Menlo Park, CA (US); William Albert Cuevas, San Francisco, CA (US)

(73) Assignee: Genencor International, Inc., Alto, CA (US)

( * ) Notice: Subject to any disclaimer, the term of this patent is extended or adjusted under 35 U.S.C. 154(b) by 641 days.

(21) Appl. No.: 10/441,908

(22) Filed: May 20, 2003

(65) Prior Publication Data

US 2004/0039179 A1 Feb. 26, 2004

Related U.S. Application Data

(60) Provisional application No. 60/381,928, filed on May 20, 2002.

(51) Int. Cl.
C07K 17/00 (2006.01)
C07K 7/08 (2006.01)

(52) U.S. Cl. .................. 530/345; 530/326; 530/327

(58) Field of Classification Search ............... None
See application file for complete search history.

(56) References Cited

U.S. PATENT DOCUMENTS

| | | | |
|---|---|---|---|
| 5,243,038 | A | 9/1993 | Ferrari et al. |
| 5,679,543 | A | 10/1997 | Lawlis |
| 6,004,444 | A | 12/1999 | Aksay et al. |
| 6,184,348 | B1 | 2/2001 | Ferrari et al. |
| 6,228,248 | B1 | 5/2001 | Aksay et al. |
| 6,365,661 | B1 | 4/2002 | Fischer et al. |
| 6,365,877 | B1 | 4/2002 | Chen et al. |
| 2001/0013294 | A1 | 8/2001 | Bruno et al. |
| 2001/0027570 | A1 | 10/2001 | Blees |

FOREIGN PATENT DOCUMENTS

| | | |
|---|---|---|
| WO | WO 97/32892 | 9/1997 |
| WO | WO 00/35993 | 6/2000 |
| WO | WO 01/46213 A2 | 6/2001 |
| WO | WO 01/87825 A1 | 11/2001 |

OTHER PUBLICATIONS

Deming, Facile synthesis of block copolypeptides of defined architecture, Nature, vol. 390, Nov. 27, 1997, pp. 386-389.
Fan, et al., Rapid prototyping of patterned functional nanostructures, Nature, vol. 405, May 4, 2000, pp. 56-60.
Brott et al., Ultrafast holographic nanopatterning of biocatalytically formed silica, Nature, vol. 413, Sep. 20, 2001, pp. 291-293.
Huo et al., Generalized synthesis of periodic surfactant/Inorganic composite materials, Nature, vol. 368, Mar. 24, 1994, pp. 317-321.
Zhou et al, Efficient Catalysis of Polysiloxane Synthesis by Silicatein α Requires Specific Hydroxy and Imidazole Functionalities, Angew. Chem. Inst., Ed. 1999, 38, No. 6, pp. 779-782.
Gosline et al., Elastic proteins: biological roles and mechanical properties, The Royal Society, Feb. 28, 2002, pp. 121-132.
Kröger et al., Polycationic Peptides from Diatom Biosilica That Direct Silica Nanosphere Formation, Science, vol. 286, Nov. 5, 1999, pp. 1129-1132.
Naik et al., Silica-Precipitating Peptides Isolated from a Combinatorial Phage Display Peptide Library, Journal of Nanoscience and Nanotechnology, 2002, vol. 2. No. 1, pp. 95-100.
Kröger et al, Silica-precipitating Peptides from Diatoms, The Chemical Structure of Silaffin-1A From Cylindrotheca Fusiformis, J. Biol. Chem., vol. 276, Issue 28, 26066-26070, Jul. 13, 2001, pp. 1-12.
Mizutani et al., Silicic Acid Polymerization Catalyzed by Amines and Polyamines, Bull. Chem. Soc. Jpn., 71, 2017-2022 (1998).
Mizutani et al., Silicic Acid Polymerization Catalyzed by Amines and Polyamines, Chemistry Letters, 1998 pp. 133-134.
Hartgerink et al., Peptide-amphiphile nanofibers: A versatile scaffold for the preparation of self-assembling materials, PNAS, Apr. 16, 2002, vol. 99, No. 8, pp. 5133-5138.
Zhang, Emerging biological materials through molecular self-assembly, Elsevier, Biotechnology Advances 20 (2002) pp. 321-339.
Wong et al., Assembly of Nanoparticles into Hollow Spheres Using Block Copolypeptides, Nano Letters, vol. 0, No. 0, pp. A-E.
Naik et al., Silica-Precipitating Peptides Isolated from a Combinatorial Phage Display Peptide Library, Journal of Nanoscience and Nanotechnology, 2002, vol. 2., No. 1, pp. 95-100.
Arkles, Commerical Applications of Sol-Gel-Derived Hybrid Materials, Mrs Bulletin, May 2001, pp. 402-408.
Sarikaya, Biomimetics: Materials fabrication through biology, PNAS, Dec. 7, 1999, vol. 96, No. 25, pp. 14183-14185.
Alvarez, Engineering Protein Molecules for the Ordered Structuring of Silica, National Nanofabrication Users Network, pp. 82-83.
Coradin et al., Biogenic Silica Patterning: Simple Chemistry or Subtle Biology? ChemBioChem 2003, 3, pp. 1-9.

*Primary Examiner*—Anish Gupta
(74) *Attorney, Agent, or Firm*—Dinsmore & Shohl LLP

(57) ABSTRACT

Methods for forming peptide derivatives using functional moieties and peptide derivatives are provided. Further, methods for using peptide derivatives to form silicon-based composite materials and silicon-based composite materials formed thereby are provided. The silicon-based composite materials may have features on the nanoscale, and the materials may exhibit characteristics derived from the functional moieties on the peptide derivatives. It is emphasized that this abstract is provided to comply with the rules requiring an abstract which will allow a searcher or other reader to quickly ascertain the subject matter of the technical disclosure. It is submitted with the understanding that is will not be used to interpret or limit the scope or meaning of the claims.

8 Claims, 8 Drawing Sheets

PEPTIDE DERIVATIVES, AND THEIR USE FOR THE SYNTHESIS OF SILICON-BASED COMPOSITE MATERIALS

CROSS REFERENCE TO RELATED APPLICATION

This application claims priority to U.S. Provisional Application No. 60/381,928, filed May 20, 2002.

BACKGROUND OF THE INVENTION

The present invention relates to the formation of peptide derivatives and to their use in the formation of functional silicon-based composite materials.

Silicon-based materials, such as silica ($SiO_2$) and silicone resins, are used in a wide array of applications, and there is growing interest in materials ordered at the nanoscale. The ability to order silicon-based materials on a nanoscale with organic templates such as polymers and surfactants provides opportunities to produce organic-inorganic hybrid composite materials having a variety of uses (Hou et al., Nature (1994), 368, 317-321).

Chemical synthesis of these materials generally requires harsh conditions involving extremes of temperature or pH. It has been recognized that amines and polyamines may catalyze the polycondensation of silicic acid in water to form a silica composite (Mizuntani et al., Bull. Chem. Soc. Jpn. (1998) 71, 2017-2022; Mizuntani et al., Chem. Lett. (1998), 133-134). More recently, the problems of chemical synthesis have been addressed using biological or biochemical synthesis techniques. The art has recognized that certain proteins and peptides are able to produce highly ordered biosilicates under ambient conditions (Zhou et al., Angew. Chem. Int. Ed. (1999) 38, 780-782). One particular class of peptides, the silaffins which are found in diatoms (Kroger et al., Science (1999) 286, 1129-1132; Kroger et al., J. Biol. Chem. (2001) 276, 26066-26070) have been observed to produce silica nanospheres and have recently been exploited in the production of optical materials (Brott et al., Nature (2001) 413, 291-293).

There remains a need in the art to provide additional silicon-based hybrid materials.

SUMMARY

The present invention meets that need by providing peptides that have been modified with at least one functional group. The peptides may be utilized as templates in the formation of silicon-based hybrid materials. The resulting silicon-based hybrid materials will have the functionality imparted by the functional group or groups on the peptides.

In accordance with an embodiment of the present invention a method of forming a composite material is provided. The method comprises providing a peptide having at least two amino acids. At least one amino acid has a polar functionality, and the peptide is substantially pure. The method further comprises modifying the peptide with a first functional moiety to form a peptide derivative and exposing the peptide derivative to a precursor containing a silicon species such that a composite material forms, wherein the peptide derivative and the silicon species are incorporated into said composite material.

In accordance with another embodiment of the present invention a method of forming a peptide derivative is provided. The method comprises providing a peptide having at least five amino acids. At least one amino acid has a polar functionality. The peptide has at least one motif comprising SGS, and the motif is flanked by an amino acid selected from a basic amino acid or an aromatic amino acid. The peptide is substantially pure. The method further comprises modifying the peptide with a first functional moiety to form a peptide derivative, wherein the peptide derivative has characteristics derived from the first functional moiety.

In accordance with yet another embodiment of the present invention a material comprising a composite material having a peptide derivative portion and a silicon containing portion is provided. The peptide derivative comprises a peptide modified with a functional moiety, and the peptide comprises at least two amino acids. At least one of said amino acids has a polar functionality. The composite material exhibits a functionality derived from the functional moiety.

In accordance with an embodiment of the present invention a peptide derivative comprising a peptide modified with a functional moiety is provided. The peptide has at least five amino acids, and the peptide comprises at least one motif. The motif comprises SGS flanked by an amino acid selected from a basic amino acid and an aromatic amino acid containing species. The peptide has less than about 45 amino acids, and the peptide has a pI greater than about 6.5.

BRIEF DESCRIPTION OF THE SEVERAL VIEWS OF THE DRAWINGS

The following detailed description of the preferred embodiments of the present invention can be best understood when read in conjunction with the following drawings, in which.

DETAILED DESCRIPTION OF THE PREFERRED EMBODIMENTS

Figure 1A:
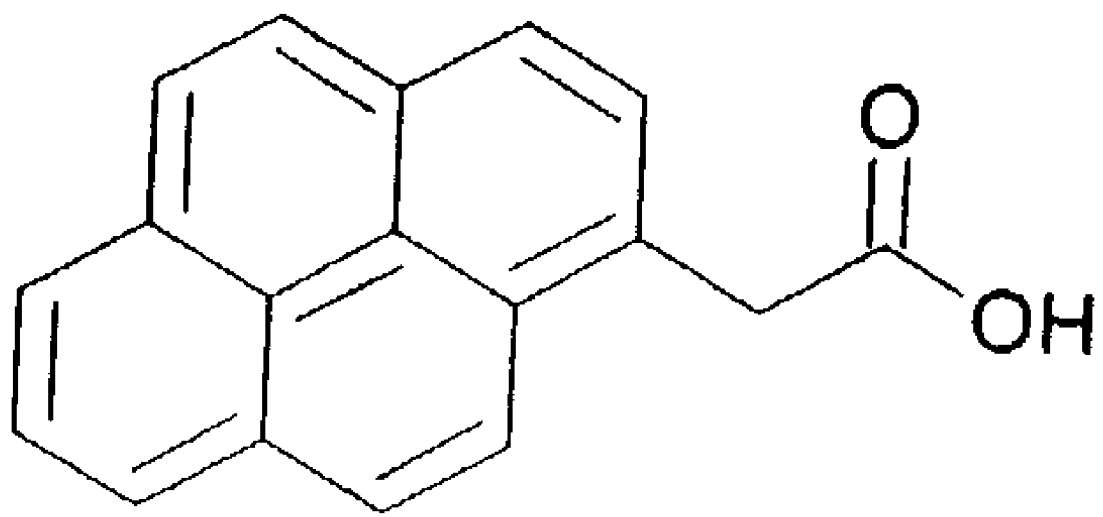
FIGS. 1A-1H represent functional moieties that may be used in embodiments of the present invention.

The present invention involves the modification of peptides to form peptide derivatives and the use of peptide derivatives to produce composite materials having desired characteristics.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical value, however, inherently contains certain errors necessarily resulting from error found in their respective measurements.

The peptides of the present invention are amino acid based materials that contain a plurality of amino acids, for example, at least 2, at least 5, or at least 7 amino acids. For example, the peptides may have less than about 45 amino acids or about 7 to about 30 amino acids. The amino acids may be the same repeating amino acids, for example, polyarginine. The peptides may be polypeptides including homopolymers. The peptides of the present invention may generally contain amino acids having polar functionality including lysine, histidine, arginine, serine, tyrosine, threonine, asparagine, glutamine, glycine and cysteine. These amino acids may bind to silicon through hydrogen bonding and ionic interactions, and the polar amino acids thus facilitate the formation of composites as discussed herein. For example, the peptide chain may contain at least one basic amino acid selected from lysine, histidine, and arginine or combinations thereof.

The peptides are generally peptides of defined amino acid sequence, and, therefore, the peptides are substantially pure. For purposes of defining and describing the present invention, "substantially pure" shall be understood as referring to peptides that comprise at least about 90% of a single peptide of defined amino acid sequence. For example, the peptide may be about 95% or about 97% of a single peptide of defined amino acid sequence. The peptides may be individual substantially pure peptides or mixtures thereof. In accordance with another embodiment of the present invention, the peptides may be substantially monodispersed. The term substantially monodispersed peptide means a peptide having a narrow molecular weight distribution. By narrow molecular weight distribution it is meant the peptides have a polydispersity of Mw/Mn between 1.00 to 1.04. In another embodiment of the present invention, the polydispersity is between 1.00 to 1.03. $M_n$ is the number average molecular weight, and it is equal to $[\Sigma(N_i)(M_i)]/[\Sigma(N_i)]$, where $N_i$ is the number of molecules of molecular weight $M_i$. $M_w$ is the weight average molecular weight, and it is equal to $[\Sigma(N_i)(M_i)^2]/[\Sigma(N_i)(M_i)]$. Molecular weight and polydispersity can be determined by tandem GPC/light scattering in 0.1 M lithium bromide in dimethylformamide at 60° C. using dn/dc values (c=concentration) measured in this solvent at $\lambda_0$=633 nm.

In accordance with an embodiment of the present invention, the peptides may contain at least one motif of serine-glycine-serine (SGS) flanked by an amino acid selected from a basic amino acid, such as lysine, arginine, and histidine, or an aromatic amino acid. Flanked shall be understood as referring to having an amino acid that may be a basic amino acid or an aromatic amino acid adjacent to each S in the SGS motif. In accordance with another embodiment of the present invention, the peptides may have at least one incidence of two or more tandem repeat polar functional amino acids. Tandem repeat amino acids shall be understood as referring to the same amino acid occurring in adjacent positions. It will be understood that the peptides may also have the motif SGS and at least one incidence of two or more tandem repeat amino acids having polar functionality. In accordance with another embodiment of the present invention, the peptides are polybasic. By polybasic it is meant the peptide comprises at least two basic amino acid residues. For example, the peptides may have a pI of greater than about 6.5. In a further example, the peptides may have a pI of between about 7 to about 12. In another example, the peptides may have a pI of between about 8 to about 12.

Examples of suitable peptides include, but are not limited to, R5 (SEQ ID NO: 1), R2 (SEQ ID NO: 2), P1 (SEQ ID NO: 3), P2 (SEQ ID NO: 4), P3 (SEQ ID NO: 5), P4 (SEQ ID NO: 6), P5 (SEQ ID NO: 7), R1 (SEQ ID NO: 16), R4 (SEQ ID NO: 17), Si3-3 (SEQ ID NO: 18), Si3-4 (SEQ ID NO: 19), Si3-8 (SEQ ID NO: 20), Si4-1 (SEQ ID NO: 21), Si4-3 (SEQ ID NO: 22), Si4-7 (SEQ ID NO: 23), Si4-8 (SEQ ID NO: 24), and Si4-10 (SEQ ID NO: 25).

R5 (SEQ ID NO: 1) has a sequence of SSKKSGSYSG-SKGSKRRIL (S=serine; K=lysine; G=glycine; Y=tyrosine; R=arginine; I=isoleucine; L=leucine) and represents the backbone sequence of the naturally occurring silaffin-1A$_1$ peptide (Kroger et al., Science (1999) 286, 1129-1132). However, synthetic R5 (SEQ ID NO: 2) does not have lysine modifications as found in the naturally occurring silaffin-1A$_1$ from diatoms. R2 (SEQ ID NO: 2) represents a variation on the backbone sequence of silaffin-1A$_2$, a naturally occurring peptide, has a sequence of SSKKSGSYSGYSTKKSG-SRIL (T=threonine) and differs from the naturally isolated peptide in its lack of one arginine residue and the posttranslational modifications of lysine. P1 (SEQ ID NO: 3) has a sequence of LDAQERRRERRAEKQEQWKAAN (D=Aspartic Acid; A=alanine, Q=Glutamine; E=Glutamic Acid; W=tryptophan; N=Asparagine) and is derived from the RNA binding N-protein (Legault et al. Cell (1998) 93, 289-299). P2 (SEQ ID NO: 4) has a sequence of SSHKSG-SYSGSHGSHRRIL and is not a naturally occurring peptide. P3 (SEQ ID NO: 5) has a sequence of CSKKSGSYSGSKG-SKRRCL, and P3 may be cyclized or uncyclized. P4 (SEQ ID NO: 6) has a sequence of SKKSGSKKSGSKKSGIL and is not a naturally occurring peptide. P5 has a sequence of RRRRRRRRR (SEQ ID NO: 7) and is modified by Ahx to be Ahx-RRRRRRRRR (Ahx=2-aminohexanoic acid).

R1 has a sequence of SSKKSGSYYSYGTKKSGSYS-GYSTKKSASRRIL (SEQ ID NO: 16) and represents the backbone sequence of the naturally occurring silaffin peptide (Kroger et al., Science (1999)286,1129-1132). R4 has a sequence of SSKKSGSYSGSKGSKRRNL (SEQ ID NO: 17) and represents the backbone sequence of the naturally occurring silaffin peptide (Kroger et al., Science (1999) 286, 1129-1132).

Si3-3 has a sequence of APPGHHHWHIHH (SEQ ID NO: 18). Si3-4 has a sequence of MSASSYASFSWS (SEQ ID NO: 19). Si3-8 has a sequence of KPSHHHHHTGAN (SEQ ID NO: 20). Si4-1 has a sequence of MSPHPH-PRHHHT (SEQ ID NO: 21). Si4-3 has a sequence of MSPHHMHHSHGH (SEQ ID NO: 22). Si4-7 has a sequence of LPHHHHLHTKLP (SEQ ID NO: 23). Si4-8 has a sequence of APHHHHPHHLSR (SEQ ID NO: 24). Si4-10 has a sequence of RGRRRRLSCRLL (SEQ ID NO: 25). Si3-3 to Si4-10 (SEQ ID NO: 18-25) are random 12 amino acid peptides derived from a combinatorial library (Naik et al., J. Nanosci. Nanotech., 2002, Vol. 2, No. 1, 95-97).

In accordance with another embodiment of the present invention, a portion of the primary structure of the sil1p protein may be used as the peptides of the present invention. Silp1 has a sequence of: MKLTAIFPLLFTAVGYCAAQ-SIADLAAANLSTEDSKSAQLISADSSDDASDSSVE SVDAASSDVSGSSVESVDVSGSSLESVD- VSGSSLESVDDSSEDSEEEELRILSS KKSGSYYSYGT-KKSGSYSGYSTKKSASRRILSSKKSG-SYSGYSTKKSGSRRILS SKKSGSYSGSKGSKRRILSSKKSGSYSG-SKGSKRRNLSSKKSGSYSGSKGSK RRILSSKKSG-SYSGSKGSKRRNLSSKKSGSYSGSKG- SKRRILSGGLRGSM (SEQ ID NO: 26) (Kroger et al., Science (1999) 286, 1129-1132). Subfragments of the sil1 P sequence having at least 2, at least 5, or at least 7 amino acids may be used in accordance with the present invention.

The peptides of the present invention are generally produced according to well known synthetic methods (Fields, G. B. (ed.) Methods in Enzymology, Volume 289: Solid-Phase Peptide Synthesis (1997) Academic Press). For example, the peptides may be produced using standard solid-phase chemistry on an automated peptide synthesizer, such as an Applied Biosystems (Foster City, CA) 433A automated peptide synthesizer.

The peptides of the present invention are modified with at least one functional moiety, for example, a single or a plurality of functional moieties, to form a peptide derivative.

As used herein, the term "modified" is defined to mean the covalent attachment of at least one functional moiety to a peptide at a predefined location. As used herein, the term "predefined location" is defined to mean a specific desired residue position within the peptide. For example, pyrene moieties may be attached to the two glutamines of SEQ ID NO: 3. As used herein, the term "functional moiety" is defined to include any species that imparts its characteristics to the molecule to which it is attached, including the impartation of chemical or physical behaviors. Therefore, the peptide derivative may have characteristics derived from the functional moiety, as may any resulting material incorporating the peptide derivative. Desirable functional moieties include, but are not limited to, dyes, tracers, chemical indicators, fluorophores, luminophores, biomolecules, biologically active compounds, enzymes, liquid crystals, enzyme inhibitors, metal chelators, metal complexes, nanoparticles, quantum dots, radioisotopes, drugs and the like. Additionally, amino acids that may influence the structure of the peptide and act in a functional manner may be functional moieties. For example, cysteine has the ability to allow the peptide to be cyclized and may act as a metal chelator. It will be understood that any functional moiety may be used for which a suitable chemical method for covalently attaching the functional moiety to the peptide exists. Alternatively, any functional moiety may be used for which a suitable biological method for covalently attaching the functional moiety to the peptide exists. Some examples of suitable biological and chemical methods are provided herein. In accordance with one embodiment, the functional moieties are attached to the peptides by solid phase chemistry.

The peptides of the present invention may generally be derivatized with at least one functional moiety. For example, the peptides may contain one to three functional moieties. When the peptide contains at least two functional moieties, the first functional moiety may be the same as or different from the subsequent functional moieties. Additionally, the first functional moiety may have the same or a different function than the subsequent functional moieties. The functional moieties may be attached to any amino acid in the peptide through methods detailed in the art (Hermanson G. T., Bioconjugate Techniques (1996) Academic Press).

Figure 1B:
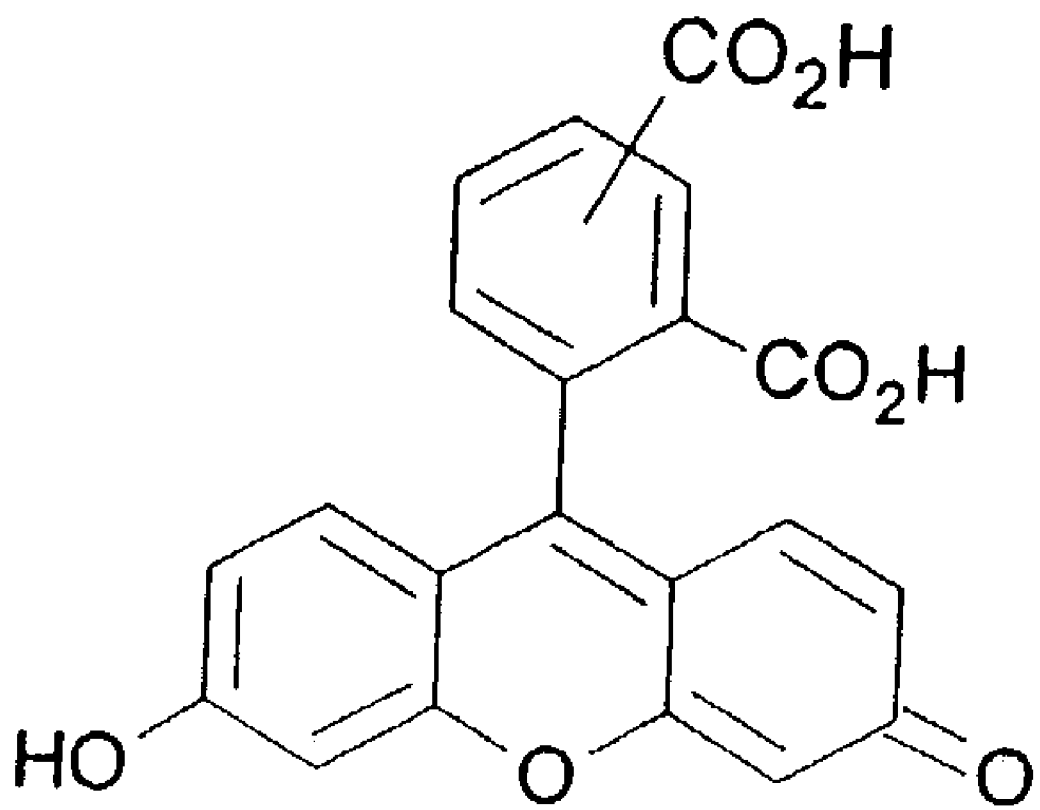

For example, suitable functional moieties include fluorophores such as pyrene and fluorescein. Other suitable fluorophores may be found in the Handbook of Fluorescent Probes and Research Products, 9$^{th}$ Ed (Molecular Probes, Eugene, Oreg.). Labeling the peptide with a fluorophore such as pyrene or fluorescein alters the optical properties of the peptide and also may influence the morphology of composites derived from the peptide derivative. The optical properties of the fluorophore and the influence of this moiety on the morphology of the nanocomposites are not necessarily related. The peptide may be labeled using 1-pyreneacetic acid as shown in FIG. 1A or 5(6)-carboxyfluorescein as shown in FIG. 1B. 1-pyrenemethylamine may also be used to label the peptide.

For example, R5 (SEQ ID NO 1) may have pyrene or fluorescein labels attached to the N-terminus. Similarly, P1 (SEQ ID NO 3) may have pyrene labels on the glutamates. The labeled glutamates may be LDAQERRRERRAEKQ EQWKAAN (SEQ ID NO: 3) where the labeled glutamates are indicated by underlining. Similarly, a fluorescein label may be attached to the N-terminus of an Ahx modified P5 (SEQ ID NO 7), and composites derived from this peptide derivative may be useful in gene and protein delivery to cells because the peptide derivative has the ability to traverse cell membranes (Futaki et al. Bioconjugate. Chem. (2001) 12, 1005-1011).

Other suitable functional moieties include enzymes such as subtilisin or β-lactamase. Once the peptide-enzyme derivative has been incorporated into a composite material, the composite may posses enzymatic activity. For example, subtilisin may be attached to the R5 peptide (SEQ ID NO 1). Similarly, the R5 peptide (SEQ ID NO 1) could be attached to the enzyme β-lactamase.

Figure 1C:
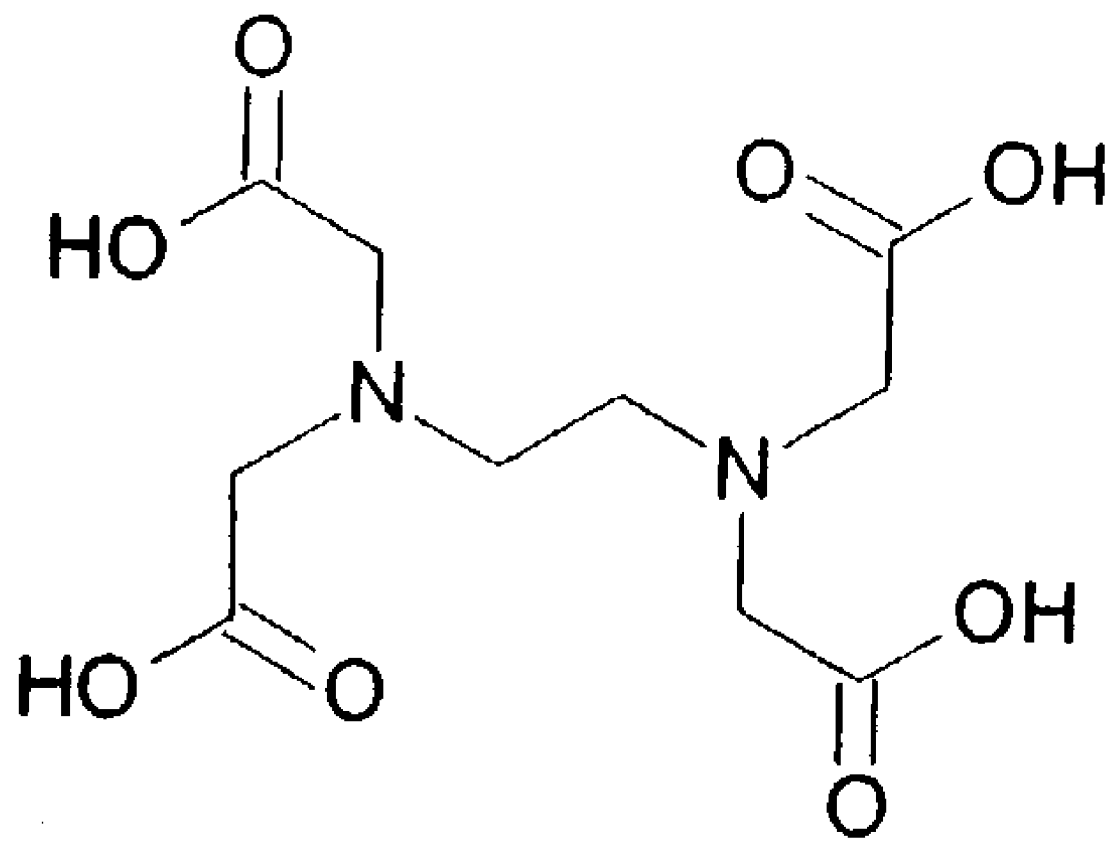
Figure 1D:
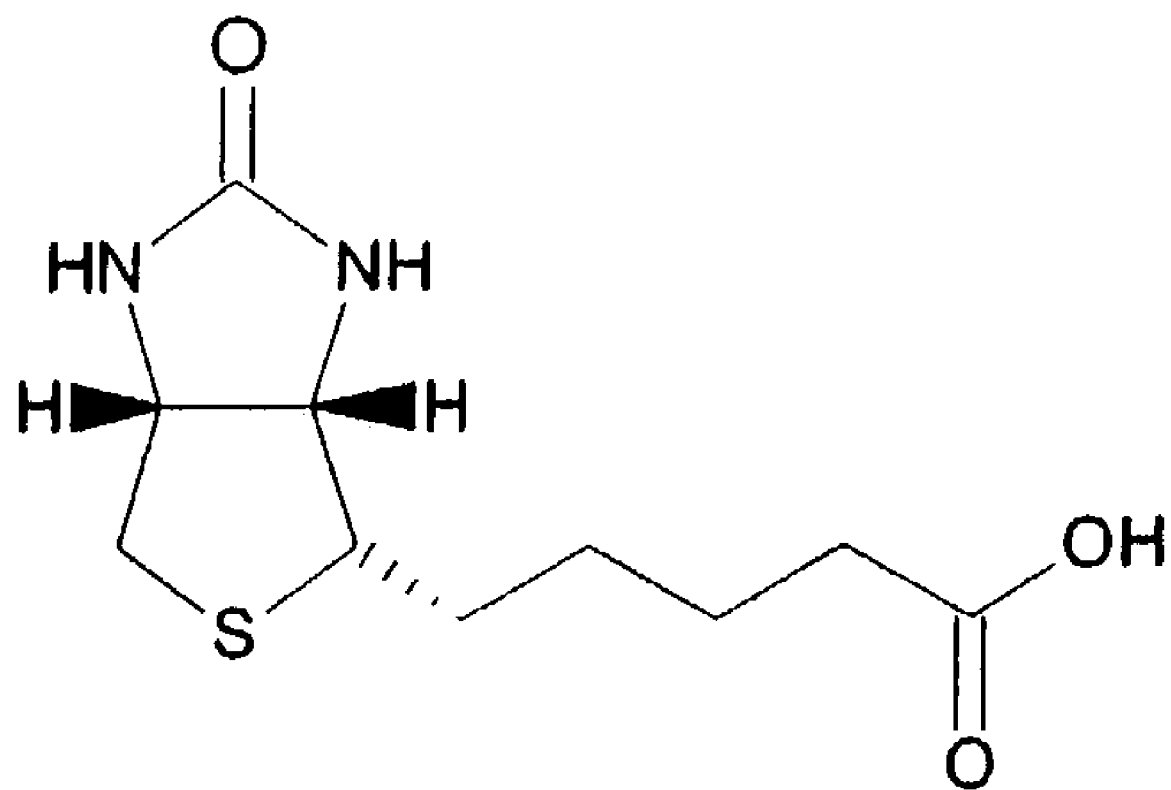
Figure 1E:
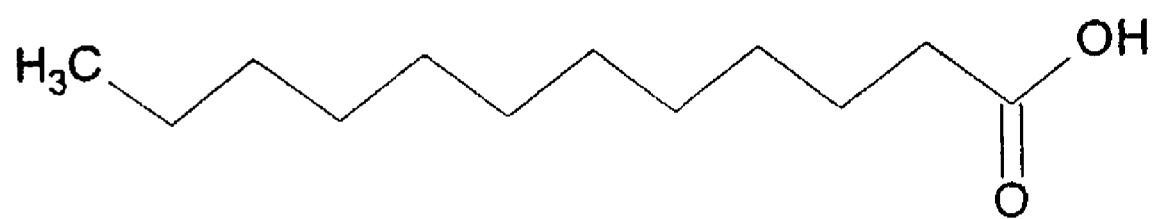
Figure 1F:
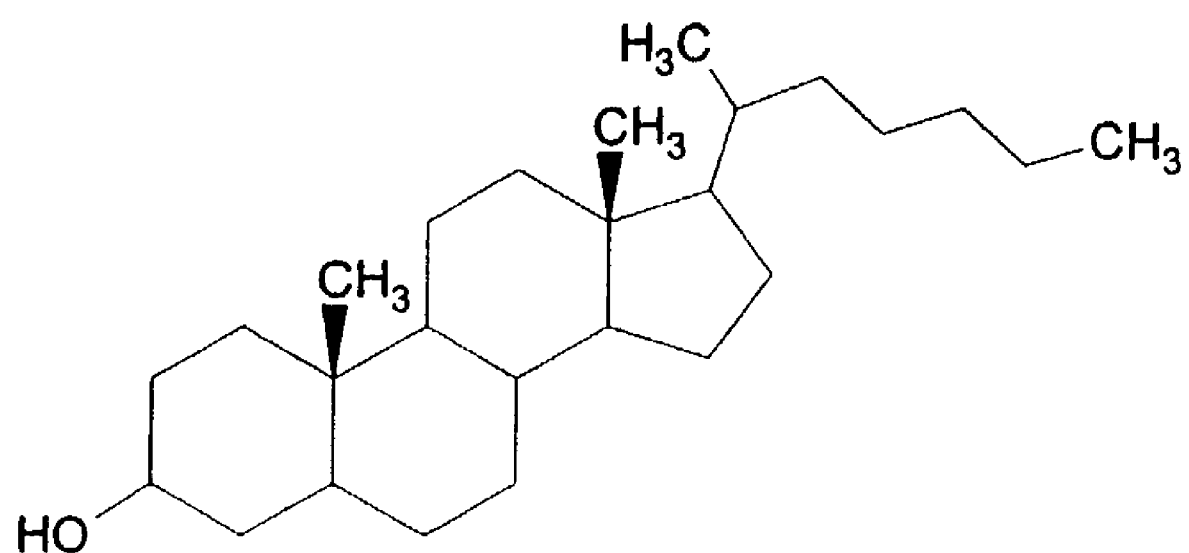

Another suitable functional moiety includes moieties that may impart hydrophobic or amphiphilic functionality. For example, saturated or unsaturated long chain fatty acids ($C_6$-$C_{22}$) may be used. One such fatty acid is lauric acid as shown in FIG. 1E. Perhydrocyclopentaphenanthrene derivatives may also provide the function of increased hydrophobicity. Steroids with 8-10 carbon atoms in the side chain at position 17 and an alcoholic hydroxyl group at position 3 are also suitable. For example cholesterol, as shown in FIG. 1F, is a suitable steroid (White, et al Principles of Biochemistry, Fifth Edition, pp 78-85). For example, the moieties may modify the physical properties, such as surfactant properties or the physical morphology, of the peptide derivative and resulting composite materials. Lauric acid may be attached to the P4 peptide (SEQ ID NO 6). In a further example, the N-terminus of P4 (SEQ ID NO 6) may be labeled with cholesterol.

Figure 1G:
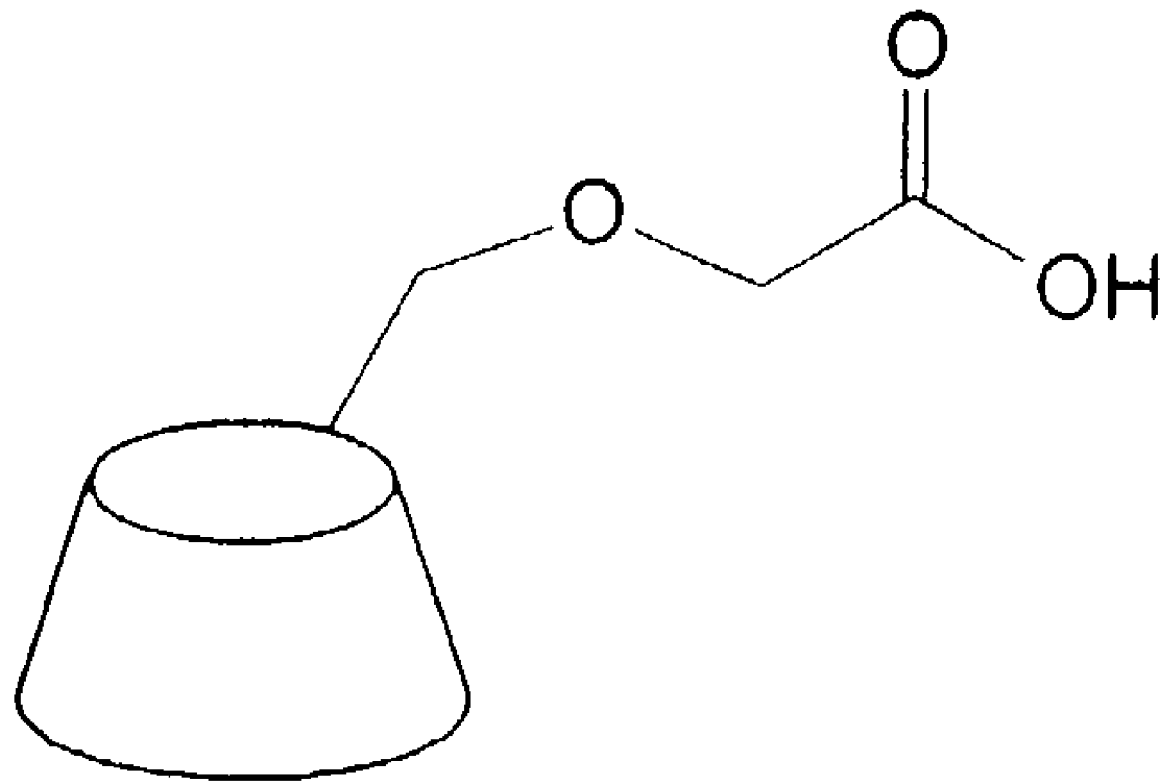
Figure 1H:
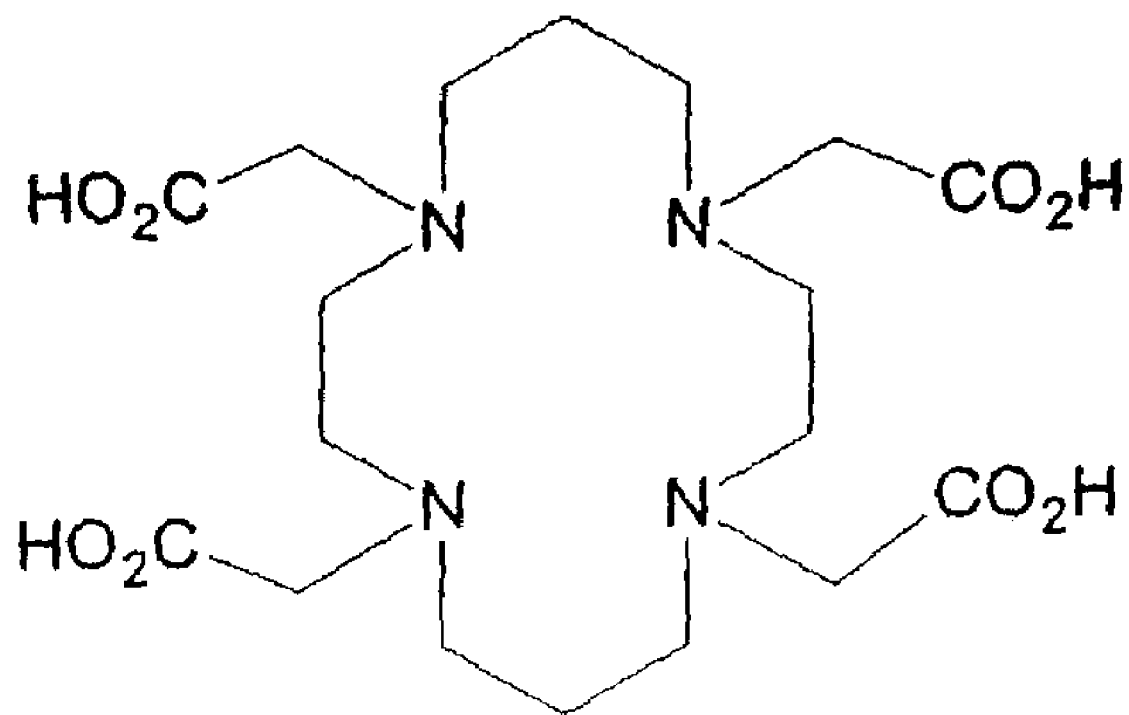

Suitable functional moieties include chelating agents. For example, suitable chelating agents include, but are not limited to porphyrins such as, porphine, heme and chlorophyll; vitamin B12, and dimercapol. Other suitable chelating agents include cyclam tetraacetic acid, as shown in FIG. 1H, and EDTA as shown in FIG. 1C. The chelating agents may impart metal chelating activity to the peptide derivatives. For example, cyclam tetraacetic acid may be added to the R5 (SEQ ID NO 2) peptide to produce a peptide derivative with metal chelating activity.

Another functional moiety may impart a protein binding ability as a possible site for the attachment of proteins. D-biotin, as shown in FIG. 1D, may be a suitable functional moiety, and the D-biotin is a known ligand for proteins (biotin binding proteins, for example, avidin and/or streptavidin). For example, the N-terminus of P4 (SEQ ID NO 6) may be labeled with D-biotin. Carboxymethyl-β-cyclodextrin, as shown in FIG. 1G, may be a suitable functional moiety, and carboxymethyl-β-cyclodextrin may provide the peptide derivative with the ability to encapsulate hydrophobic guest molecules (D'Souza, V. T., Lipkowitz, K. B. Chemical Reviews (1998), 98, 1741-1742). For example, carboxymethyl-β-cyclodextrin may be added to the R5 peptide (SEQ ID NO 1).

The functional moieties may be added to the peptides using chemical or biological methods. For example, the functional moieties may be added chemically while the peptide is still on the resin after automated peptide synthesis. The substitution of the peptide on the resin is generally calculated manually or by using software, such as software available under the tradename SYNTHASSIST® software from Applied Biosystems (Foster City, Calif.). The groups protecting the amino acids to be substituted are removed, and the resin is swelled in a solvent such as N-methyl-2-pyrrolidone (NMP) prior to the addition of the precursor containing the functional moiety. The functional moiety is added to the resin slurry, and the reaction is allowed to proceed. The reaction may be promoted by additional reagents or catalysts, including enzymes, depending on the nature of the desired chemical functionality linking the peptide and the functional moiety. The nature of these chemical fuctionalities includes but is not limited to amides, esters, acetals, ketals, ethers, amines, thioethers, thioesters, imines, phosphate esters, carbon-carbon bonds, silicon-carbon bonds, silicon-oxygen bonds and the like. After the reaction, the solid phase is typically washed, and the modified peptide is cleaved, deprotected, and purified in accordance with well-known methods. However, the functional moieties may be added after cleavage and deprotection of the peptide. In this instance, the unprotected peptide is dissolved in a suitable solvent and attached to the functional moiety in a similar fashion as described for resin-bound peptides. If multiple products result from such treatment then one can improve the chemical selectivity of the coupling reaction through methods described in the art (Hermanson G. T., Bioconjugate Techniques (1996) Academic Press) or apply a suitable technique for purification of the desired conjugate following the reaction.

Alternatively, the entire peptide derivative comprising a peptide and at least one functional moiety may be generated using molecular biology techniques. This approach is particularly useful for attaching a functional moiety such as a protein. In this approach, a DNA sequence encoding the peptide is inserted into the DNA sequence of the desired functional moiety. The insertion of a DNA sequence encoding the peptide into a DNA sequence encoding the desired functional moiety may be accomplished using well known vector and fusion techniques. The peptide may then be expressed by inserting the recombinant DNA into a host cell for replication and expression. U.S. Pat. No. 5,679,543, the disclosure of which is herein incorporated by reference, contains a number of references to articles that outline suitable recombinant DNA techniques. Additionally, Jeremy Thorner et al., Applications of chimeric genes and hybrid proteins: Part A: Gene Expression and Protein purification (Methods in Enzymology, vol. 326) (2000) contains suitable methods for forming fusion proteins and is incorporated by reference herein.

Once the peptide derivative has been formed, it is exposed to a precursor containing a silicon species, and the peptide derivative acts as a template in the formation of a silicon-based composite. Ordinarily, the peptide derivative does not serve as a catalyst. Rather, the peptide derivative becomes incorporated into the composite to form a hybrid material comprising the peptide derivative and the silicon containing species. The composite material may be nanostructured in the form of nanoparticles or aggregates thereof. Nanoparticles are distinct clusters or spheres of material of diameter between about 1 and about 1000 nm. Other morphologies are also possible however, including fibers, laminates, gels, crystalline materials, porous solids and materials with features on several distinct length scales from nanometers to centimeters.

The silicon species in the precursor may be in any suitable form. For example, silicates or organosilanes may be the silicon species. For example, the silicon species may be in the form of a Q-, T-, D- or M-unit silicate and silane or mixtures thereof. Q-unit silanes have a silicon-containing group of the general structure $SiO_4$— (four points of attachment). T-unit silanes have a silicon-containing group of the general structure —$RSiO_3$— (three points of attachment) where R represents any group containing carbon. D-unit silanes have a silicon-containing group of the general structure —$R_2SiO_2$— (two points of attachment). M-unit silanes have a silicon-containing group of the general structure —$R_3SiO$—. Examples of suitable precursors include, but are not limited to inorganic Q units such as orthosilicic acid ($Si(OH)_4$), its salts and oligomers, organic Q units such as tetramethoxysilane (TMOS), tetraethoxysilane (TEOS), T-units such as phenyltriethoxysilane, phenyltrichlorosilane, 3-aminopropyltriethoxysilane, methyltrimethoxysilane, D-units such as phenylmethyldichlorosilane, dimethyldimethoxysilane and M-units such as trimethylchlorosilane. These silane precursors may be pretreated to maximize the silanol (Si—OH) content through either chemical or enzymatic hydrolysis. For example, treatment of tetraethoxysilane (TEOS) in 1 mM hydrochloric acid (HCl) results in a solution of orthosilicic acid over several hours suitable for composite preparation.

The peptide derivative is generally exposed to the silicon precursor in solution at a pH of between about 5 to about 10. For example, a pH of between about 6 to about 9 may be used. In a further example, a pH between about 7 to about 8 may be used. The peptide derivative is generally exposed to the silicon precursor at ambient temperature and pressure.

The peptide derivative may be exposed to the silicon precursor solution in bulk. The peptide derivative may alternatively be exposed to the silicon precursor by slow addition or addition under dilute conditions in order to alter the morphology of nanoparticles. In another alternative, the peptide derivative may be exposed to the silicon precursor in the presence of a suitable surfactant in order to alter the morphology of nanoparticles. Additionally, the Stober process may be utilized to promote monodispersity of, prevent aggregation of, or otherwise alter the morphology of nanoparticles (Stober et al., *Stober Process for Controlled Particle Growth*, E. J. Colloid Interface Sci., 26, 62 (1968)). Alternately, the peptide derivative and silane precursor may be mixed in a two phase system comprising two immiscible solvents.

For example, the exposure of peptide derivatives in solution to a silicic acid solution may produce a composite material of silica and peptide, which may be in the form of a gel or solid material. By "gel or solid" it is meant a gel or solid being about 50% or less aqueous or organic solvent by weight. The composite material may also be in the form of aggregates, fibers, laminates, and the like. In a further example, the exposure of the peptide derivatives to an organosilane such as a T-, D-, or M-unit silane may produce a composite material of organosilane and peptide derivative. The composites may be 3-dimensional networks containing organosilane units and peptide units. Such composite materials may be useful in the formation of thin-films, coatings, and the like. Thus, the composite materials may be hybrid materials that have both inorganic and organic components.

Further treatment of the composite may provide new materials wherein the organic portion of the composite is altered. For example, the organic portion may be crosslinked or removed. Exemplary methods of alteration include electromagnetic irradiation, thermal treatment and/or chemical treatment. For example, a composite could be constructed containing a reactive functionality. Such functionality might originate from either a modified peptide template or the silane precursor. Subsequent crosslinking of the reactive functionality could result from treatment of the composite by irradiation, chemical or thermal treatment. Another example might involve the removal of all or part of the organic portion of a composite by high temperature thermal treatment (i.e. calcination). Such treatment could result in the formation of composites with increased porosity and/or altered morphology as compared to the untreated composites.

It may be possible to form patterned structures by using the peptide derivative to form a pattern on any suitable substrate and exposing the pattern to the silicon-containing precursor. Soft lithography is a non-photolithographic technique useful for carrying out micro- and nanofabrication. Soft lithography may produce patterns and structures having feature sizes ranging from about 30 nm to about 100 μm. Soft lithography generally utilizes an elastomeric stamp or mold with patterned relief structures on its surface used to generate the desired pattern. In one embodiment, an elastomeric stamp may be formed using a master mold. The stamp is "inked" with the peptide derivative in a solution and a substrate is contacted with the stamp. A pattern of peptide derivative is formed on the substrate in the areas where the relief structures of the stamp contacted the substrate. Examples of suitable soft lithographic stamps are found in published U.S. Patent Application Nos. 20010027570 and 20010013294, the disclosures of which are incorporated by reference herein. Alternatively, a mold may be formed and placed in contact with a substrate. A peptide derivative solution is then placed at one end of the mold, and channels in the mold fill by capillary action to form a pattern after the mold is removed. Additionally, the substrate itself may be patterned by soft lithography, and the peptide derivative may then be applied to the substrate to fill the pattern. For example, placing a mold on the substrate and filling it with a prepolymer may pattern the substrate. U.S. Pat. No. 6,368,877 discloses several methods of forming patterns using soft lithography and is incorporated by reference herein.

In rapid printing, a self assembling "ink" comprising the peptide derivative in solution is used with rapid printing procedures to form patterned structures in a very short period of time. Suitable rapid printing procedures include pen lithography, ink-jet printing, and dip-coating. The rapid printing procedures use the ink to form a desired pattern on suitable substrates. The ink thus forms patterned peptide derivatives that define functional, hierarchically organized structures in seconds. Suitable rapid printing techniques and apparatus are described in Hongyou Fan, *Rapid Prototyping of Patterned Functional Nanostructures*, Nature 405, 56-60 (2000), which is incorporated by reference herein. Three-dimensional structures may be formed on a suitable substrate by forming the peptide pattern, exposing the pattern to a silicon-containing precursor, and repeating the procedure until the desired structure has been achieved.

In accordance with another embodiment of the present invention, the nanocomposites of the present invention may be formed in an electric or magnetic field to provide control over the morphology of the nanocomposite materials. Additionally, the nanocomposites may be formed in a porous matrix to provide control over the morphology of the nanocomposite. The peptide derivative may be exposed to a suitable precursor in the presence of any suitable electric or magnetic field. For example, the peptide derivative may be provided in an agarose matrix and standard gel electrophoresis equipment may be used to provide an electric field during the exposure of the peptide derivative. In a further example, a peptide derivative with a metal-chelating group may be attached to magnetic particles, and the nanocomposite formation may be performed in an electric field. For example, the magnetic particles may be pulled through a silicate solution at an appropriate pH. The electromagnetic parameters and peptide/functional moieties may all be controlled to direct the morphology of the resulting nanocomposites.

In order that the invention may be more readily understood, reference is made to the following examples, which are intended to be illustrative of the invention, but are not intended to be limiting in scope.

EXAMPLE 1

The R5 (SEQ ID NO: 1), P4 (SEQ ID NO: 6), and P1 (SEQ ID NO: 3) base sequences were created using standard Fmoc chemistry on an Applied Biosystems 433A automated peptide synthesizer. For each base sequence, 137 mg of ABI preloaded Fmoc Wang (HMP) resin was used. Subsequent offline cleavage and deprotection of 100 mg resin with attached peptide was performed in a cleavage solution contained 1110 μL trifluoroacetic acid (TFA), 30 μL water, 30 μL triisopropylsilane (TIS), and 30 μL 1,2-ethanedithiol (EDT), for a total volume of 1200 μL. The reaction was allowed to run 3-4 hours, and the deprotected peptide was then filtered from the resin into 10 mL ice-cold (0° C.) methyl-tert-butyl ether (MtBE). The peptide was centrifuged in MtBE at 4900 rpm for 5 minutes, the MtBE poured off, and the peptide then resuspended in fresh MtBE. This was cycle was repeated four times and the peptide was then allowed to dry and submitted for HPLC analysis. Purification was performed by preparative HPLC using a Vydac C18 column (22 mm by 250 mm) and eluted with a gradient of water (0.1% TFA) and acetonitrile (0.08% TFA). Fractions containing the desired material were pooled and lyophilized to yield the pure peptide. Identity was confirmed by mass spectrometry.

EXAMPLE 2

The P3 (SEQ ID NO: 5) peptide sequence was cyclized. The P3 peptide was synthesized using normal Fmoc chemistry on an automated peptide synthesizer in accordance with Example 1. P3 peptide (65.6 mg) was cleaved from the resin and then cyclized by forming the cysteine-cysteine disulfide bridge. This cyclization was induced using EKATHIOX resin, made by Ekagen (Menlo Park, Calif.) and distributed by Sigma-Aldrich (St. Louis, Mo.). A ten-fold molar excess of resin active group (0.35 mmol/g, 1.0 gram EKATHIOX) was stirred with the peptide in 33 mL deionized water with 0.5% (v/v) acetic acid for approximately 48 hours. The EKATHIOX was then filtered from the solution and the peptide was lyophilized. Cyclization was confirmed by MALDI-TOF mass spectrometric analysis, including a 50/50 mixture of treated and untreated P3 showing two corresponding peaks

EXAMPLE 3

Labeling of the N-terminus of the R5 (SEQ ID NO: 1) sequence with fluorescein was performed while the peptide was still on the resin and its side chain amino acid groups were still protected, herein referred to as R5-resin. The final Fmoc removal from the N-terminus was performed on the automated peptide synthesizer. The substitution of peptide on resin was calculated by Applied Biosystems SynthAssist®software software, and 105 mg R5-resin contained 23.1 μmol peptide. The 105 mg of R5-resin was swollen in 500 μL N-methylpyrrolidone (NMP) for five minutes in a frifted filtration vessel. About 25 equivalents of diisopropylethlamine (DIEA), 285 μL (2 M) DIEA in NMP, was added to the R5-resin, and then 70 mg (152 μmol) 5-carboxyfluorescein was added. The reaction was protected from light and allowed to mix in excess of 24 hours. The solid phase was then washed twice with NMP and four times with dichloromethane (DCM) before being dried under nitrogen. The peptide was cleaved and deprotected as described in Example 1.

EXAMPLE 4

Labeling of the N-terminus of the R5 (SEQ ID NO: 1) sequence with pyrene was performed while the peptide was still on the resin and its side chain amino acid groups were still protected, herein referred to as R5-resin. The final Fmoc removal from the N-terminus was performed on the automated peptide synthesizer. The substitution of peptide on resin was calculated by software sold under the tradename SYNTHASSIST® software by Applied Biosystems (Foster City, Calif.), and 100 mg R5-resin contained 22.6 µmol peptide. The 100 mg of R5-resin was swollen in 500 µL NMP for five minutes in a fritted filtration vessel. Concurrently, 35.3 mg (135.6 µmol) pyreneacetic acid (PAA) was dissolved in 1 mL dimethylsulfoxide (DMSO). After swelling of the resin, 250 µL (0.5 M) HBTU/HOBt solution was added to the R5-resin and allowed to mix for 10 minutes. The next step was to add 150 µL (2 M) DIEA to the pyreneacetic acid solution. The PAA solution containing DIEA was added to the R5-resin slurry and the reaction mixed for 20-30 minutes. The solid phase was then washed twice with DMSO, twice with NMP, and three times with DCM before being dried under nitrogen. The peptide was cleaved and deprotected as described in Example 1.

EXAMPLE 5

Two glutamatic acid residues of P1 (SEQ ID NO: 3) were labeled with pyrene. The automated synthesis of P1 (SEQ ID NO: 3) used two glutamatic acid residues protected by 2-phenylisopropylester (PiPE) groups and retained the Fmoc on the N-terminus. The PiPE groups were removed by mixing 300 mg P1-resin with a solution of 2% TFA and 5% TIS in DCM. The P1-resin was mixed three times with 3 mL of deprotecting solution for 3-4 minutes each time. A fritted filtering vessel was used to expedite this process. The solid phase was then washed twice with 2% TIS in DCM and three times with a 50/50 solution of DCM and methanol. After drying under nitrogen, the PiPE-deprotected P1-resin was transferred to a round bottom flask. The calculated substitution of the P1-resin was 0.139 µmol/mg, thus the 300 mg P1-resin contained approximately 83.4 µmol peptide. After swelling the resin in dimethylformamide (DMF), 17.4 mg (129 µmol) HOBt and 66.4 mg (128 µmol) pyBOP (NovaBiochem) were dissolved into the slurry. Then 250 µL (2 M) DIEA in NMP was added to the P1-resin mixture, and concurrently 113.2 mg (423 µmol) 1-pyrenemethylamine (PMA) was dissolved separately in DMSO. Both flasks were allowed to stir 10 minutes, and then the PMA in DMSO was added to the activated P1-resin. The final mixture was allowed to react for over an hour and then transferred to a fritted filtration vessel. The solid phase was washed twice with DMF, twice with DMSO, and four times with DCM, and then dried under nitrogen. The labeled glutamates are underlined in the labeled P1 (SEQ ID NO: 3) sequence LDAQERRRERRAEKQEQWKAAN.

The Fmoc on the N-terminus was removed by reacting the pyrene-labeled P1-resin in a solution of 20% piperidine in DMF for 1 hour. The solid phase was washed three times with DMF, twice with a 50/50 solution of DCM and methanol, and three times with DCM. The peptide was cleaved and the remaining side-chain protecting groups removed as described in Example 1.

EXAMPLE 6

The N-terminus of the P4 (SEQ ID NO: 6) sequence was labeled with lauric acid. The labeling was performed while the peptide was still on the resin and its side chain amino acid groups were still protected, herein referred to as P4-resin. The final Fmoc removal from the N-terminus was performed on the automated peptide synthesizer. Substitution of peptide on resin was calculated by Applied Biosystems software. P4-resin (83 mg, 22.7 µmol peptide) was swollen in 500 µL NMP for five minutes. Concurrently, 28 mg (137 µmol) lauric acid, $CH_3(CH_2)_{10}COOH$, was dissolved in 1 mL dimethylformamide (DMF), and then 1300 µL (0.1 M in DMF) HBTU/HOBt solution was added to the lauric acid. The next step was to add 150 µL (2 M) DIEA to the lauric acid mixture and allow it to stir. Then the solution containing lauric acid, HBTU/HOBt, and DIEA was added to the P4-resin slurry and the reaction mixed for at least one hour. The solid phase was then washed twice with NMP, twice with DMF, and four times with dichloromethane (DCM) before being dried under nitrogen. The peptide was cleaved and deprotected as described in Example 1.

EXAMPLE 7

The N-terminus of the P4 (SEQ ID NO: 6) sequence is labeled with carboxymethyl β-cyclodextrin (CMβCD). The labeling is performed while the peptide is still on the resin and its side chain amino acid groups are still protected, herein referred to as P4-resin. The final Fmoc removal from the N-terminus is performed on the automated peptide synthesizer. Substitution of peptide on resin is given to be 0.22 µmol/mg. A solution of CMPCD (263 mg, 220 µmol), HOBt (28.5 mg, 211 µmol), benzotriazole-1-yl-oxy-tris-pyrrolidino-phosphonium hexafluorophosphate (pyBOP) (114.5, 220 µmol), and 500 µL (2M) DIEA in 9 mL DMSO is allowed to stir for one week. Alternatively, a solution containing cyclam tetraacetic acid or 5(6)-carboxyfluorescein may be used. Then P4-resin (200 mg, 44 µmol peptide) is swelled in 1 mL NMP and is added to the solution containing CMβCD. This final slurry is stirred overnight. The solid phase is then washed twice with DMSO, twice with DMF, and four times with DCM before being dried under nitrogen. The peptide is cleaved and deprotected as described in Example 1.

EXAMPLE 8

The R5 sequence (SEQ ID NO: 1) was labeled with pyrene. In this instance, the automated synthesis of R5 (SEQ ID NO: 1) used two lysines protected by methyltrityl (Mtt) groups and retained the Fmoc on the N-terminus. The Mtt groups were removed by stirring R5-resin in three batches of 2 mL TFA-TIS solution (1% trifluroacetic acid, 3% triisopropylsilane in DCM) for five minutes each batch. A frifted filtering vessel was used to expedite this process. The solid phase was then washed twice with 2% TIS in DCM and three times with a 50/50 solution of DCM and methanol. After drying under nitrogen, the Mtt-deprotected R5-resin was transferred to a round bottom flask. The Applied Biosystems software gave a calculated substitution of 0.20 µmol/mg. Thus, the 90 mg R5-resin contained approximately 18 µmol peptide, or 36 µmol deprotected lysine sites. The resin was swollen in 500 µL N-methylpyrrolidine (NMP). In a separate flask, 57.1 mg (216 µmol) pyreneacetic acid (PAA) was dissolved in DMSO. First 2016 µL HBTU/HOBt (0.1 M) and then 500 µL DIEA (2M in NMP) was added to the dissolved PAA and allowed to react for 10 minutes. The solution containing PM, HBTU/HOBt, and DIEA was added to the R5-resin slurry.

The final mixture was allowed to react for over an hour and then transferred to a fritted filtration vessel. The solid phase was washed three times with DMSO, twice with NMP, and four times with DCM, and then dried under nitrogen. Labeled lysines are underlined in the R5 sequence: SS KKSGSYSGSKGSKRRIL. (SEQ ID NO: 1). The Fmoc may be removed from the N-terminus of the labeled peptide in a reaction solution of 20% piperidine in DMF. The peptide may be cleaved in accordance with the procedure of Example 1.

EXAMPLE 9

The N-terminus of the P4 peptide (SEQ ID NO: 6) was labeled with cholesterol. The labeling of the N-terminus of the P4 peptide (SEQ ID NO: 6) was performed while the peptide was still on the resin and its side chain amino acid groups were still protected, herein referred to as P4-resin. The final Fmoc removal from the N-terminus was performed on the automated peptide synthesizer. The substitution of peptide on resin was estimated to be 0.20 µmol/mg, and 140 mg P4-resin contained approximately 28 µmol peptide. The 140 mg of P4-resin was mixed with 152 mg (280 µmol) cholesterol chloroformate and 420 µL (2 M) diisopropylethlamine (DIEA) in NMP, in 8-10 mL NMP total. The reaction was allowed stir at room temperature protected for 24 hours. The solid phase was then washed twice with NMP and four times with dichloromethane (DCM) before being dried under nitrogen. The peptide was cleaved and deprotected as described in Example 1. The P4-cholesterol was purified and its identity confirmed by MALDI-TOF mass spectrometry.

EXAMPLE 10

The N-terminus of the P4 peptide (SEQ ID NO: 6) was labeled with EDTA dianhydride in accordance with the following procedure. Labeling of the N-terminus of the P4 sequence (SEQ ID NO: 6) was performed while the peptide was still on the resin and its side chain amino acid groups were still protected, herein referred to as P4-resin. The P4-resin used in this experiment was synthesized by SynPep Corp. (Dublin, Calif.), lot 02GE2271, and the final Fmoc had already been removed from the N-terminus. Substitution of the peptide on resin was given to be 0.22 µmol/mg. The ethylenediaminetetraacetic acid (EDTA) dianhydride was added at approximately five equivalents to the peptide. P4-resin (100 mg, 22 µmol peptide) was swollen in N-methylpyrrolidone (NMP) and to this was added 25 mg EDTA (100 µmol) and 100 µL (2M in NMP) DIEA. The reaction was stirred for two hours and then quenched with water. The solid phase was washed twice with NMP and four times with DCM before being dried under nitrogen. The peptide-EDTA conjugate was deprotected and cleaved as described in Example 1, and the identity of the material confirmed by mass spectrometry.

EXAMPLE 11

The N-terminus of the P4 peptide (SEQ ID NO: 6) was labeled with biotin in accordance with the following procedure. Biotin was conjugated to the P4 peptide (SEQ ID NO: 6) to form Biotin-SKKSGSKKSGSKKSGIL called "P4-biotin." Labeling of the N-terminus of the P4 sequence (SEQ ID NO: 6) was performed while the peptide was still on the resin and its side chain amino acid groups were still protected, hereinafter called P4-resin. The P4-resin was synthesized by SynPep, lot 02GE2271, and the final Fmoc had already been removed from the N-terminus. The coupling reaction of biotin to peptide was achieved via standard HOBT/HBTU chemistry, such as that used in automated peptide synthesis. The peptide-biotin conjugate was deprotected and cleaved as described in Example 1.

EXAMPLE 12

The N-terminus of the P5 peptide (SEQ ID NO: 7) with an Ahx linker was labeled with fluorescein in the following manner. Labeling of the N-terminus of the P5 (SEQ ID NO: 7) with an Ahx linker sequence was performed while the peptide was still on the resin and its side chain amino acid groups were still protected, hereinafter referred to as Ahx-P5-resin. The Ahx-P5-resin used in this experiment was synthesized by SynPep, lot 027191GEN, and the final Fmoc had already been removed from the N-terminus. The substitution of peptide on resin was given to be 0.5 µmol/mg. Ahx-P5-resin (60 mg, 30 µmol) was swollen in NMP for five minutes in a fritted filtration vessel. Diisopropylethlamine (DIEA), 200 µL (2 M) DIEA in NMP, was added to the Ahx-P5-resin, and then NHS-fluorescein (60 mg, 136 µmol) was added under yellow light. The mixture was protected from light, flushed gently with nitrogen and allowed to stir for 24 hours. The solid phase was then washed three times with NMP and three times with dichloromethane (DCM) before being dried under nitrogen. The peptide was cleaved and deprotected as described in Example 1.

EXAMPLE 13

Peptide and subtilisin fusions were prepared using molecular biology methods. A *Bacillus subtilis* strain (BS 1033, Genentech) was obtained from Genencor International. This *Bacillus* strain carried the plasmid pSS5 into which the GG36 gene construct T274A was inserted. T274A (U.S. Pat. No. 5,185,258) was a modification of the original *Bacilus lentis* (ATCC 21536) GG36 protease gene in which the penultimate amino acid, threonine, had been converted to an alanine with the resulting addition of a unique PstI restriction site at this site.

As the PSS5 vector contains a PstI restriction site, T274A was transferred to vector pBS42 rending the construct amenable to using its unique PstI site the for the insertion of peptide sequences. The following oligonucleotides were custom made from Operon Technologies (Alameda, Calif.):

```
R5, upper strand:
GCTCGCTCCT CCAAAAAATC CGGTTCCTAC    (SEQ ID NO: 8)

TCCGGTTCCA AAGGTTCCAA ACGTCGTATC

CTGTAATGCA

R5, bottom strand (SEQ ID NO: 9):
TTACAGGATA CGACGTTTGG AACCTTTGGA    (Seq. ID No. 9)

ACCGGAGTAG GAACCGGATT TTTTGGAGGA

GCGAGCTGCA

R2, upper strand (SEQ ID NO: 10):
GCTCGCTCCT CCAAAAAATC CGGTTCCTAC    (Seq. ID No. 10)

TCCGGTTACT CCACCAAAAA ATCCGGTTCC

CGTATCCTGT AATGCA

R2, bottom strand (SEQ ID NO: 11):
TTACAGGATA CGGGAACCGG ATTTTTTGGT    (Seq. ID No. 11)

GGAGTAACCG GAGTAGGAAC CGGATTTTTT
```

```
-continued
GGAGGAGCGA GCTGCA

P4, upper strand (SEQ ID NO: 12):
GCTCGCTCCA AAAAATCCGG TTCCAAAAAA    (Seq. ID No. 12)

TCCGGTTCCA AAAAATCCGG TATCCTGTAA

TGCA

P4, bottom strand (SEQ ID NO: 13):
TTACAGGATA CCGGATTTTT TGGAACCGGA    (Seq. ID No. 13)

TTTTTTGGAA CCGGATTTTT TGGAGCGAGC

TGCA
```

The above oligo pairs are designed to be complimentary yielding PstI "sticky ends" when annealed. Insertion of the annealed pairs into the PstI site corresponding to the penultimate GG36 amino acid alanine results in maintaining the alanine as well as the final GG36 arginine. Peptide amino acid sequences are then encoded, in frame, followed immediately by a TM stop codon.

The above oligo pairs were mixed in equimolar amounts, 125 µM each, in water. Mixtures were heated to 90° C. for ten minutes in a heating block in Hotstart (wax containing) PCR tubes. The heating block was then switched off and allowed to cool to room temperature over the course of ~1 hour. 1 µL of annealed mixture was used in a ligation reaction with 1 µL (ca. 250 ng) of PstI cut, gel purified pBS42T274A vector. Gel analysis indicated that this resulted in an overwhelming ratio of insert to vector. A Boeringer Mannheim "Rapid Ligation" kit was used as per manufacturer's protocol. 5 µL of each ligation mix was used to transform competent E. coli MM294 cells (50 µl cells, mixed thoroughly, incubated on ice 30 min, 60 second 37° C. heat shock, 2 min. on ice, 1 hour outgrowth in 150 µL SOC at 37° C. for 1 hour, 100 µL plated to two LA-cmp5 plates). Control plates using 1 µL water in place of insert resulted in TMTC colonies while all other plates yielded 25-30 colonies each. Ten colonies from each different peptide insert transformation were picked and analyzed by PCR. One of ten colonies for the R5 and R2 constructs and three of the ten P4 constructs were shown to have the proper orientation/insertion. Correct orientation and sequences were confirmed using DNA sequencing.

EXAMPLE 14

The peptide-subtilisin fusions were expressed as proteins using the following methods. GG36-peptide fusion plasmids were isolated and used to transform Bacillus subtilis 3594 comK cells. Transformants were grown on LA-cmp5 plates containing 1.6% skim milk. Cells containing fusion plasmids as well as native GG36 (T274A) exhibited similar zones of skim milk clearing indicating the production of active protease while untransformed cells grown on antibiotic-free LA/skim milk plates did not. Single colonies of the transformants were grown in 5 ml overnight tubes containing LB-cmp5 for 9 hours at 37° C. 250 rpm (OD ~5). 50 µL of this growth was used to inoculate 50 mL of FN2 Shake Flask Medium containing 5 mg/L cmp in 250 mL fluted Erlenmeyer shake flasks. Flasks were grown at 37° C. 250 rpm. Flasks containing native GG36 (T274A) as well as media alone were included as controls. After 40 hrs growth, culture supernatants were harvested by centrifugation/filtration (0.22 µm) and concentrated ~3× using a Centricon device (10K MWCO). Centricon permeate and concentrated retentates were desalted/buffer exchanged using 25 mM tris-HCl pH 8.0 equilibrated P-10 desalting columns (Bio-Rad).

GG36-peptide construct plasmids were transformed into Bacillus subtilis strain AK2200 as previous. This is a strain that has been deleted for six post-translational modification proteases and has been used in the production of modified enzymes. Resulting transformants demonstrated skim milk clearing, however in this case the R5 and R2 constructs yielded smaller clearing zones than the control GG36 (T274A) while the P4 construct yielded barely perceptible clearing zones. Single colonies were grown in shake-flasks and their culture supernatants processed.

EXAMPLE 15

A P4 Peptide (SEQ ID NO: 6)-β-lactamase (BLA) fusion has been prepared using molecular biology methods. Plasmid pME22 containing engineered BLA was restriction digested with BbsI and gel purified. Plasmid pME22 contains the marker that confers chloramphenicol (cmp) resistance; properly expressed BLA confers resistance to cefotoxime (ctx) as well. The engineered BLA also contains a "his tag" (six histidine residues at its C-terminus) to facilitate subsequent purification. Oligonucleotide pairs were obtained as in Example 13.

The oligo pair was designed to be complimentary, yielding appropriate "sticky ends" when annealed. Insertion of the annealed pairs into the BbsI cut pME22 results in in-frame addition of peptide DNA sequences in addition to required start signal peptide sequences. Signal peptide is cleaved upon secretion of the fusion protein into the cell periplasm yielding peptides fused to active BLA. Due to the nature of BbsI cutting, pME22 cannot re-circularize and inserts that are not properly oriented or annealed will not result in in-frame expression of active fused BLA. The following oligo pair was synthesized:

```
P4-BLA, upper strand:
ACTAGTCGTT CCTTTCTATT CTCACTCTTC    (SEQ ID NO: 14)

CAAAAAATCC GGTTCCAAAA AATCCGGTTC

CAAAAAATCC GGTATCCTGA CGCCAGTGTC

AGAAAAACAG CTG

P4-BLA, lower strand:
CCGCCAGCTG TTTTTCTGACA CTGGCGTCA    (SEQ ID NO: 15)

GGATACCGGA TTTTTTGGAAC CGGATTTTTT

GGAACCGGAT TTTTTGGAAG AGTGAGAATAG

AAAGGAACG AC
```

The above oligo pair was mixed in equimolar amounts, 12.5 µM each, in water. 100 µL was heated to 100° C. for 2 minutes in a heating block in Hotstart (wax containing) PCR tubes. The heating block was switched off and allowed to cool to room temperature over the course of ~1 hour. 2.5 µL of annealed mixture was used in a ligation reaction with 2.5 µL (ca. 50 ng) of BbsI cut, gel purified pME22 plasmid. A Takara kit (Cambrex Bio Science Verviers S.P.R.L., BELGIUM) was used as per manufacturer's protocol. 5 µL of the 10 µL ligation mix was used to transform competent E. coli TOP10 (Invitrogen) cells (50 µL cells, mixed thoroughly, incubated on ice 30 min, 30 second 42° C. heat shock, outgrowth in 250 μL SOC at 37° C. for 1 hour, entire volume plated to one LA-cmp5 plates which yielded 5-10 colonies each). Five transformants were picked and tested for growth on LA plates containing cmp as well as ctx, 5 and 0.1 ppm respectively. All colonies grew in presence of ctx and were analyzed by PCR. All colonies were found to contain correct plasmid constructs by PCR; purified plasmid was used to confirm all by DNA sequencing.

EXAMPLE 16

The peptide-BLA fusion was expressed as protein using the following methods. Single colonies of the fusion constructs as well as a control BLA fusion (pME23) were grown in 5 mL overnight tubes containing LB-cmp5 overnight at 37° C. 250 rpm (OD ~5). 200 μL of this growth was used to inoculate 50 mL of TB media containing 5 mg/L cmp in 250 ml fluted Erlenmeyer shake flasks. Flasks were grown at 37° C. 250 rpm. After 24 hrs growth, culture supernatants were harvested by centrifugation/filtration (0.22 μm) and cell pellets were stored at −20° C.

Supernatants were concentrated ~3× using a Centricon device (10K MWCO). Centricon permeate and concentrated retentates were desalted/buffer exchanged using 25 mM tris-HCl pH 8.0 equilibrated P-10 desalting columns (Bio-Rad).

Periplasmic fusion protein was purified using a Pro-Bond kit (Invitrogen) optimized for the affinity purification of "his tagged" proteins as per manufacturer's protocol. Concentrated supernatants and Pro-Bond purified material was analyzed by SDS-PAGE (NuPage gels, 4-12%, MES buffer). Fusion protein appears to have its expected molecular weight as determined by MALDI-TOF mass spectrometry. N-terminal protein sequencing by Edman Degradation confirms that the fusion is mostly intact, the P4 (SEQ ID NO:6) moiety being truncated by two amino acids.

EXAMPLE 17

A nanocomposite utilizing the R5-fluorescein peptide conjugate was formed. A silicic acid solution was formed by dissolving 0.208 g (1 M) tetraethylorthosilicate (tetraethoxysilane, TEOS) in 1 mM HCl in deionized water (1 mL total) for 6-18 hours. 100 μL (1 M) silicic acid solution was added to 1 mg/mL fluorescein-R5 peptide (SEQ ID NO 1) conjugate in 900 μL (25 mM Tris-HCl) buffer, pH 8. The reaction was allowed to run for half an hour on a rotary mixer. The reaction mixture was then centrifuged at 14,000 rpm to spin down precipitate. The solution was removed with a pipette and the remaining material was mixed with deionized water and centrifuged again. Precipitate was washed at least twice in this manner, frozen at −80° C., and lyophilized. The composite was fluorescent under ultraviolet light and possessed a different morphology than the composite derived from the unlabelled R5 peptide as imaged by SEM.

EXAMPLE 18

A nanocomposite was formed from combination of a T-unit silane with fluorescein labeled P5 peptide (SEQ ID NO 7), hereinafter referred to as P5-fluorescein. A solution of 241 μL phenyltriethoxysilane (PhSi(OEt)$_3$), 234.5 μL (60 mM) HCl (aq.), and 296 μL ethanol was allowed to react for 2 hours, after which phenyltriethoxysilane was considered hydrolyzed. First 100 μL of P5-fluorescein (10 mg/mL in deionized water) was added to 800 μL Tris-HCl (25 mM) buffer, followed by 100 μL pre-hydrolyzed phenyltriethoxysilane solution. The reaction was performed in triplicate and the solutions were allowed to stir 10 minutes; the precipitated material was an orange color indicating the presence the P5-fluorescein peptide. The reactions were centrifuged at 14,000 rpm for 15 minutes, re-suspended in purified water, centrifuged again, and the pellet remaining was lyophilized. The presence of the P5-fluorescein peptide in the composite was further confirmed by mass spectrometry.

EXAMPLE 19

Peptides of the present invention were found to produce a novel product when exposed to T-unit silanes. 23.4 μL (0.1 M) 3-aminopropyltriethoxysilane or 24.1 μL (0.1 M) phenyltriethoxysilane was added directly to a 10 mM Tris-HCl buffered R5 peptide (SEQ ID NO: 1) solution (1.5-1.9 mg/mL) at either pH 7 or pH 8 for a total volume of 1 mL. The assays were allowed to run overnight on a rotary mixer. The samples, including experimental controls that lacked peptide, appeared foamy and could not be centrifuged at 14,000 rpm. All samples were frozen at −80° C. and lyophilized. Selected samples were then analyzed by SEM imaging and SEM-EDS analysis. Imaging of the precipitated material by SEM showed clear differences in morphology between control (no peptide) and experimental preparations. Whereas the control preparations were completely amorphous, the peptide-precipitated material contained square-shaped features on the order of 500 to 1000 nm.

EXAMPLE 20

A slow addition reaction to promote the monodispersity of nanoparticles is performed. A solution of 0.1 M silicic acid is made by dissolving 20.8 mg TEOS in 1 mM HCl for a total volume of 1 mL. This silicic acid solution is added incrementally to a peptide solution of 1.1 mg R5 (SEQ ID NO: 1) in 800 μL (25 mM) Tris-HCl buffer, pH 8. Aliquots of 10 μL each of the silicic acid solution are added every 30 seconds for 10 minutes, resulting in a total reaction volume of 1 mL at the end of the slow addition processes. The reaction mixture is then centrifuged at 14,000 rpm to spin down precipitate. The solution is removed with a pipette and the remaining material is mixed with deionized water and centrifuged again. The precipitate is washed at twice in this manner, frozen at −80° C., and lyophilized.

EXAMPLE 21

Nanocomposites were precipitated using a number of peptides and peptide derivatives as shown in Table 1 in accordance with the following procedure. 0.208 g (1 M) tetraethylorthosilicate (TEOS) was first dissolved in 1 mM HCl in deionized filtered water (1 mL total) for 6-18 hours to make a silicic acid solution. The assay contained 100 μL (1 M) silicic acid solution added to 100 μL (10 mg/mL) peptide in 800 μL (50 mM) sodium borate buffer, pH 8.5. The reaction was generally allowed to run for half an hour or more on a rotary mixer. The reaction mixture and controls (with unmodified peptide and without peptide) were then centrifuged at 14,000 rpm to spin down any precipitate. The supernatant was removed with a pipette and the remaining material was mixed with deionized water and centrifuged again. Precipitate was washed at least twice in this manner, frozen at −80° C., and lyophilized. The reactions were performed in duplicate. The mass of the lyophilized material recovered from each experiment is given below:

TABLE 1

| Name (+silane) | Sample 1 (+/−0.2 mg) | Sample 2 (+/−0.2 mg) |
|---|---|---|
| P4 (SEQ ID NO: 6) | 0.5 mg | 0.8 mg |
| P4-C12 | 0.4 mg | 0.5 mg |
| P4-cholest | 0.4 mg | 0.3 mg |
| P4-EDTA | less than 0.2 mg | less than 0.2 mg |
| No peptide | None observed | None observed |

EXAMPLE 22

Silica precipitation using a biotinylated P4 peptide (SEQ ID NO: 6) was performed. A 10 mg/mL solution of P4-biotin was made in deionized water. This peptide solution (100 µL, 1 mg/mL final concentration) was added to borate buffer (800 µL, 50 mM) at pH 8.5. Silicic acid, made from 1 M TEOS in 1 mM aqueous HCl stirred overnight, was added (100 µL) to the buffered peptide. A very fine precipitate was observed within the first two minutes of reaction time. The final solution, at a pH of 8.0+/−0.2, was allowed to stir at room temperature for 10 minutes before the first centrifugation. The 1 mL aliquot was spun on an ultracentrifuge for 12-15 min. at 14,000 g. The liquid was removed and the precipitate was resuspended in deionized water. The precipitate was then spun and washed twice more with deionized water.

EXAMPLE 23

Q/T-unit mixed-resin composites were formed with silica-precipitating peptides as shown in Table 2. 29 µL (~0.02 M) methyltrimethoxysilane and 184 µL (0.08 M) tetraethylorthosilicate were dissolved in 1 mM HCl in deionized filtered water (1 mL total) for 6-18 hours to make a homogenous solution of mixed Q/T prehydrolyzed solution. 100 µL (1 M) of the mixed Q/T prehydrolyzed solution added to 100 µL (10 mg/mL) peptide in 800 µL (50 mM) sodium borate buffer, pH 8.5. The reactions were allowed to run 10 minutes on a rotary mixer. The reaction mixture and controls (with unmodified peptide and without peptide) were then centrifuged at 14,000 rpm to spin down any precipitate. The supernatant was removed with a pipette and the remaining material was mixed with deionized water and centrifuged again. Precipitate was washed at least twice in this manner, frozen at −80° C., and lyophilized.

The mass of the lyophilized material recovered from each experiment is given below:

TABLE 2

| Name (+Q/T) | Sample 1 (+/−0.2 mg) |
|---|---|
| P4 (SEQ ID NO: 6) | 0.3 mg |
| P4-C12 | 2.2 mg |
| P4-cholesterol | 0.7 mg |
| P4-EDTA | less than 0.2 mg |
| No peptide | None observed |

EXAMPLE 24

The ability to modify a surface using the peptide derivatives of the present invention was confirmed. Glass microscope slides were cleaned by treatment with a solution of ethanolic KOH (3 M) for 10 minutes followed by sequential washing with 1 M Tris-HCl, pH 8 and deionized water. The labeled peptides R5-fluorescein and R5-pyrene were applied to the treated glass surface in two ways. In the first method, the glass slide was dip coated in a peptide solution (10 mg/mL). The second method used a solution of peptide (10 mg/mL) in ethanol, which was applied manually in several layers, allowing the ethanol to evaporate between layers. In both cases, the presence of the peptide film was visually confirmed by examining the glass slides under UV light.

A silicic acid solution as described in Example 13 was then spotted onto the peptide film with a pipette tip. After five minutes, the slides were washed several times by vigorous agitation in deionized water. The spots containing the peptide-silica nanocomposite adhered to the glass slide and showed fluorescence under UV light, whereas the unreacted peptide film was no longer present. Controls using buffer (25 mM Tris-HCl, pH 8) instead of silicic acid solution did not result in peptide retention on the surface following the final wash. To demonstrate the potential for surface patterning with this technique, the silicic acid solution was applied to the peptide film in a series of dots resulting in the formation of a peptide/silica composite array.

EXAMPLE 25

The P5-fluorescein-silica nanocomposite as made in Example 18 was used to label Daudi cells. Aliquots (1-2 mg) of both the P5-fluorescein peptide and the P5-fluorescein-silica nanocomposite were resuspended in PBS buffer (1.2 ml) containing 0.05% bovine serum albumin (BSA) and centrifuged to remove unsuspended solids. Daudi Cells ($7 \times 10^7$ total), obtained from the ATTC (Manassas, Va.) and cultured under recommended conditions, were mixed with the peptide ligands and incubated for 2.5 hr at 37° C. in 3 ml of PBS/BSA buffer. The total fluorescence of the solutions was measured and expressed in terms of relative fluorescence units (RFU). Controls for ligands with no cells, and cells with no ligand were run in parallel. Duplicate tests were run for cells with ligands and single tests were run for others. The RFU levels of the control samples with ligand alone were subtracted from the ligand plus cell samples. Following incubation, cells were washed twice in 10 ml PBS/BSA buffer, resuspended in 2.6 ml buffer and two aliquots of 0.2 ml were assayed. Fluorescence measurements of the cell fraction indicated that the P5-fluorescein peptide alone bound poorly to the cells (0.16 RFU, 0.07% of total RFU added), whereas the P5-fluorescein-silica nanocomposite bound 14-fold more efficiently (7.8 RFU, 1% of total RFU).

EXAMPLE 26

A silica nanocomposite was synthesized with pyrene labeled peptides mediated by an electric field. The R5-pyrene peptide as formed in example 8 was contacted with a silicate solution in 50 mM borate buffer, pH 8.0 in a 0.5% agarose matrix under the influence of an electric field as follows. Standard gel electrophoresis equipment was used and the gel matrix was 0.5% agarose. A small well (50-100 $mm^2$) was cut into the agarose matrix in the experimental lane near the negative electrode and filled with a 1 M sodium silicate solution, pH 8.5 which had been freshly prepared by dilution of a 6.25 M stock solution with deionized water and pH adjustment with Amberlite IRA-118, H$^+$ resin. A corresponding well in the control lane contained 50 mM sodium borate buffer, pH 8.0. Similar wells nearest to the positive electrode contained 200 μL each of the R5-pyrene peptide (10 mg/mL). A middle well in each lane contained 50 mM sodium borate buffer, pH 8.0. A potential (120 V) was applied across the electrodes and the peptide bands (control and experimental) were observed under UV light to move through the gel toward the negative electrode. The peptide in the control lane moved continuously in a narrow band. The peptide in the experimental lane was arrested and then appeared to spread out, after which no movement was observed in the experimental lane. Observation of the experimental lane under a fluorescence microscope revealed the formation of dispersed fluorescent particles embedded within the agarose matrix, the size of which were estimated to be in the 100-200 nm range. Such particles were not observed in the control lane.

What is claimed is:

1. A method of forming a composite material comprising:
providing a peptide selected from those having amino acid sequences of substantially SSKKSGSYSGSKG-SKRRIL (SEQ ID NO: 1), SSKKSGSYSGYSTKKSG-SRIL (SEQ ID NO: 2), LDAQERRRERRAEKQEQW-KAAN (SEQ ID NO: 3), SSHKSGSYSGSHGSHRRIL (SEQ ID NO: 4), CSKKSGSYSGSKGSKRRC (SEQ ID NO: 5), SKKSGSKKSGSKKSGIL (SEQ ID NO: 6), RRRRRRRRR (SEQ ID NO 7) with an aminohexanoic acid linker, SKKSGSYYSYGTKKSGSYS-GYSTKKSASRRIL (SEQ ID NO: 16), SKKSGSYSG-SKGSKRRNL (SEQ ID NO: 17), PPGHHHWHIHH (SEQ ID NO: 18), MSASSYASFSWS (SEQ ID NO: 19), KPSHHHHHTGAN (SEQ ID NO: 20), MSPH-PHPRHHHT (SEQ ID NO: 21), MSPHHMHHSHGH (SEQ ID NO: 22), LPHHHHLHTKLP (SEQ ID NO: 23), APHHHHPHHLSR (SEQ ID NO: 24), and RGR-RRRLSCRLL (SEQ ID NO: 25);

modifying said peptide with a first functional moiety selected from the group consisting of 1-pyreneacetic acid, 1-pyrenemethylamine, 5(6)-carboxyfluorescein, EDTA, cyclam tetraacetic acid, lauric acid, cholesterol, D-biotin, carboxymethyl-β-cyclodextrin, and cysteine to form a peptide derivative; and exposing said peptide derivative to a precursor containing a silicon species such that a composite material forms, wherein said peptide derivative and said silicon species are incorporated into said composite material.

2. The method of claim 1 wherein said peptide comprises substantially SSKKSGSYSGSKGSKRRIL (SEQ ID NO: 1).

3. The method of claim 1 wherein said peptide comprises substantially SSKKSGSYSGYSTKKSGSRIL (SEQ ID NO: 2).

4. The method of claim 1 wherein said peptide comprises substantially LDAQERRRERRAEKQEQWKAAN (SEQ ID NO: 3).

5. The method of claim 1 wherein said peptide comprises substantially SSHKSGSYSGSHGSHRRIL (SEQ ID NO: 4).

6. The method of claim 1 wherein said peptide comprises substantially CSKKSGSYSGSKGSKRRC (SEQ ID NO: 5).

7. The method of claim 1 wherein said peptide comprises substantially SKKSGSKKSGSKKKSGIL (SEQ ID NO: 6).

8. The method of claim 1 wherein said peptide comprises substantially RRRRRRRRR (SEQ ID NO: 7) with an aminohexanoic acid linker.

* * * * *

UNITED STATES PATENT AND TRADEMARK OFFICE
CERTIFICATE OF CORRECTION

PATENT NO. : 7,361,731 B2 Page 1 of 1
APPLICATION NO. : 10/441908
DATED : April 22, 2008
INVENTOR(S) : Joseph C. McAuliffe, Risha Bond and Bill Cuevas It is certified that error appears in the above-identified patent and that said Letters Patent is hereby corrected as shown below:

Col. 12, line 29 "CMPCD" should read as --CMßCD--

Col. 15, line 22 "TM" should read as --TAA--

Col. 34, line 8 "SKKSGSKKSGSKKKSGIL" should read as --SKKSGSKKSGSKKSGIL--

Signed and Sealed this

Sixteenth Day of December, 2008

JON W. DUDAS
*Director of the United States Patent and Trademark Office*

SEQUENCE LISTING

<160> NUMBER OF SEQ ID NOS: 26

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ser Lys Lys Ser Gly Ser Tyr Ser Gly Ser Lys Gly Ser Lys Arg
 1               5                  10                  15

Arg Ile Leu

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ser Lys Lys Ser Gly Ser Tyr Ser Gly Tyr Ser Thr Lys Lys Ser
 1               5                  10                  15

Gly Ser Arg Ile Leu
            20

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Asp Ala Gln Glu Arg Arg Arg Glu Arg Arg Ala Glu Lys Gln Glu
 1               5                  10                  15

Gln Trp Lys Ala Ala Asn
            20

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ser His Lys Ser Gly Ser Tyr Ser Gly Ser His Gly Ser His Arg
 1               5                  10                  15

Arg Ile Leu

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Ser Lys Lys Ser Gly Ser Tyr Ser Gly Ser Lys Gly Ser Lys Arg
 1               5                  10                  15

Arg Cys Leu

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Lys Lys Ser Gly Ser Lys Lys Ser Gly Ser Lys Lys Ser Gly Ile
 1               5                  10                  15

Leu

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Arg Arg Arg Arg Arg
 1               5

<210> SEQ ID NO 8
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctcgctcct ccaaaaaatc cggttcctac tccggttcca aggttccaa acgtcgtatc      60 ctgtaatgca                                                           70

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttacaggata cgacgtttgg aacctttgga accggagtag gaaccggatt ttttggagga      60
gcgagctgca                                                           70

```
<210> SEQ ID NO 10
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gctcgctcct ccaaaaaatc cggttcctac tccggttact ccaccaaaaa atccggttcc    60
cgtatcctgt aatgca                                                   76

<210> SEQ ID NO 11
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttacaggata cgggaaccgg attttttggt ggagtaaccg gagtaggaac cggatttttt    60
ggaggagcga gctgca                                                   76

<210> SEQ ID NO 12
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gctcgctcca aaaatccgg ttccaaaaaa tccggttcca aaaatccgg tatcctgtaa     60 tgca                                                                64

<210> SEQ ID NO 13
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttacaggata ccggattttt tggaaccgga ttttttggaa ccggattttt tggagcgagc    60
tgca                                                                64

<210> SEQ ID NO 14
<211> LENGTH: 103
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
actagtcgtt cctttctatt ctcactcttc caaaaaatcc ggttccaaaa atccggttc     60 caaaaaatcc ggtatcctga cgccagtgtc agaaaaacag ctg                    103

<210> SEQ ID NO 15
<211> LENGTH: 103
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 15
ccgccagctg tttttctgac actggcgtca ggataccgga ttttttggaa ccggattttt      60
tggaaccgga ttttttggaa gagtgagaat agaaaggaac gac                       103

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ser Lys Lys Ser Gly Ser Tyr Tyr Ser Tyr Gly Thr Lys Lys Ser
 1               5                  10                  15

Gly Ser Tyr Ser Gly Tyr Ser Thr Lys Lys Ser Ala Ser Arg Arg Ile
                20                  25                  30

Leu

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ser Lys Lys Ser Gly Ser Tyr Ser Gly Ser Lys Gly Ser Lys Arg
 1               5                  10                  15

Arg Asn Leu

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Pro Pro Gly His His His Trp His Ile His His
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Ser Ala Ser Ser Tyr Ala Ser Phe Ser Trp Ser
 1               5                  10

<210> SEQ ID NO 20
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 20

Lys Pro Ser His His His His Thr Gly Ala Asn
 1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Ser Pro His Pro His Pro Arg His His His Thr
 1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Ser Pro His His Met His His Ser His Gly His
 1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Pro His His His His Leu His Thr Lys Leu Pro
 1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Pro His His His His Pro His His Leu Ser Arg
 1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gly Arg Arg Arg Arg Leu Ser Cys Arg Leu Leu
 1               5                   10
```

-continued

```
<210> SEQ ID NO 26
<211> LENGTH: 265
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Lys Leu Thr Ala Ile Phe Pro Leu Leu Phe Thr Ala Val Gly Tyr
 1               5                  10                  15

Cys Ala Ala Gln Ser Ile Ala Asp Leu Ala Ala Ala Asn Leu Ser Thr
            20                  25                  30

Glu Asp Ser Lys Ser Ala Gln Leu Ile Ser Ala Asp Ser Ser Asp Asp
        35                  40                  45

Ala Ser Asp Ser Ser Val Glu Ser Val Asp Ala Ala Ser Ser Asp Val
    50                  55                  60

Ser Gly Ser Ser Val Glu Ser Val Asp Val Ser Gly Ser Ser Leu Glu
 65                  70                  75                  80

Ser Val Asp Val Ser Gly Ser Ser Leu Glu Ser Val Asp Asp Ser Ser
                85                  90                  95

Glu Asp Ser Glu Glu Glu Leu Arg Ile Leu Ser Ser Lys Lys Ser
            100                 105                 110

Gly Ser Tyr Tyr Ser Tyr Gly Thr Lys Lys Ser Gly Ser Tyr Ser Gly
        115                 120                 125

Tyr Ser Thr Lys Lys Ser Ala Ser Arg Arg Ile Leu Ser Ser Lys Lys
    130                 135                 140

Ser Gly Ser Tyr Ser Gly Tyr Ser Thr Lys Lys Ser Gly Ser Arg Arg
145                 150                 155                 160

Ile Leu Ser Ser Lys Lys Ser Gly Ser Tyr Ser Gly Ser Lys Gly Ser
                165                 170                 175

Lys Arg Arg Ile Leu Ser Ser Lys Lys Ser Gly Ser Tyr Ser Gly Ser
            180                 185                 190

Lys Gly Ser Lys Arg Arg Asn Leu Ser Ser Lys Lys Ser Gly Ser Tyr
        195                 200                 205

Ser Gly Ser Lys Gly Ser Lys Arg Arg Ile Leu Ser Ser Lys Lys Ser
    210                 215                 220

Gly Ser Tyr Ser Gly Ser Lys Gly Ser Lys Arg Arg Asn Leu Ser Ser
225                 230                 235                 240

Lys Lys Ser Gly Ser Tyr Ser Gly Ser Lys Gly Ser Lys Arg Arg Ile
                245                 250                 255

Leu Ser Gly Gly Leu Arg Gly Ser Met
            260                 265
```